(12) United States Patent
Gao et al.

(10) Patent No.: US 7,659,408 B2
(45) Date of Patent: Feb. 9, 2010

(54) PYRAZOLE CARBOXAMIDES AS INHIBITORS OF 11-β-HYDROXYSTEROID DEHYDROGENASE-1

(75) Inventors: Ying-Duo Gao, Edison, NJ (US); Xin Gu, Scotch Plains, NJ (US); Nancy J. Kevin, East Brunswick, NJ (US); Sherman T. Waddell, Westfield, NJ (US)

(73) Assignee: Merck Sharp & Dhome Corp., Rahway, NJ (US)

( * ) Notice: Subject to any disclaimer, the term of this patent is extended or adjusted under 35 U.S.C. 154(b) by 470 days.

(21) Appl. No.: 10/567,141

(22) PCT Filed: Aug. 3, 2004

(86) PCT No.: PCT/US2004/025036

§ 371 (c)(1),
(2), (4) Date: Feb. 6, 2006

(87) PCT Pub. No.: WO2005/016877

PCT Pub. Date: Feb. 24, 2005

(65) Prior Publication Data

US 2008/0153893 A1    Jun. 26, 2008

Related U.S. Application Data

(60) Provisional application No. 60/493,487, filed on Aug. 7, 2003.

(51) Int. Cl.
*A61K 31/4155* (2006.01)
*A61K 31/4525* (2006.01)
*C07D 231/16* (2006.01)
*C07D 401/06* (2006.01)
*C07D 403/06* (2006.01)

(52) U.S. Cl. .................... 548/374.1; 514/406
(58) Field of Classification Search .............. 548/374.1
See application file for complete search history.

(56) References Cited

U.S. PATENT DOCUMENTS 4,950,668 A * 8/1990 Okada et al. ............. 514/232.2
5,258,397 A   11/1993 Lepage et al.

FOREIGN PATENT DOCUMENTS

| GB | 1209326 | * | 10/1970 |
| WO | WO-01/29007 A1 | * | 4/2001 |
| WO | WO 03/020217 A2 | | 3/2003 |
| WO | WO 2004/089470 A2 | | 10/2004 |
| WO | WO 2005/095350 A1 | | 10/2005 |
| WO | WO 2005/108359 A1 | | 11/2005 |

OTHER PUBLICATIONS

Bizzi et al., CA 67:98714, 1967.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*
CA Registry No. 515831-42-2, indexed in the Registry file on STN May 15, 2003.*
CA Registry No. 515830-06-5, indexed in the Registry file on STN May 15, 2003.*
CA Registry No. 515829-57-9, indexed in the Registry file on STN May 15, 2003.*
CA Registry No. 515120-36-2, indexed in the Registry file on STN May 14, 2003.*
Nakaya et al., CA 79:42548, 1973.*
Seltzman et al., CA 137:370019, Mar. 2002.*
Guerry, Philippe et al., Database CA, "Preparation of 2, 4-diaminopyrimidine derivatives as antibacterially-active medicaments", XP-002516494, Database accession No. 1997:752949; WO 97/43277A1 (Hoffman-La Roche), 1997.
Maslivets, A. N. et al., Database CA. "Five-membered 2,3-dioxo heterocycles. VIII. Reaction of 1-aryl-4-aroyl-5-methoxycarbonyl-2,3-dihydro-2,3-pyrrolediones with secondary aliphatic amines", XP-002516493, Database accession No. 1989:423322, Zhurnal Organicheskoi Khirnii (1988), 24(10), pp. 2205-2212.
Andreichokov, Yu S. et al.. Database CA, "Ring cleavage of 2,5-dihydro-3,5-dihydroxy-2-pyrrolone by hydrazine to give a pyrazolecarboxanilide", XP-002516492, Database accession No. 1988:528887, Zhurnal Organicheskoi Khirnii (1987), 23(10), pp. 2254-2255.
Garthwaite, Gitti et al., Database CA, "Preparation of pyrazoles and indazoles for blockading voltage dependent sodium channels", XP-002516491, Database accession No. 2001:581875, WO 01/57024 (University College, London), 2001.
Huppatz, John L., et al., Database CA, "Structure-activity relationships in a series of fungicidai pyrazolecarboxanilides", XP-002516490, Database accession No. 1984:116332, Agricultural and Biological Chemistry (1984), 48(1), pp. 45-50.
Fadl, T. A. Abo-El et al., Database Crossfire Beilstein, "1,5-Dimethyl-1H-pyrazole-3-carboxylic acid benzylamide", XP-002516489, Registry No. 6649389, Pharmazie, 48, No. 2, 1993, pp. 117-120.
Fadl, T. A. Abo-El et al., Database Crossfire Beilstein, "1,5-Dimethyl-1H-pyrazole-3-carboxylic acid cyclohexylamide", XP-002516488, Registry No. 6647597, Pharmazie, 48, No. 2. 1993, pp. 117-120.

* cited by examiner

*Primary Examiner*—Laura L. Stockton
(74) *Attorney, Agent, or Firm*—Mark R. Daniel; Heidi M. Struse

(57) ABSTRACT

Pyrazole carboxamides of structural formula I are selective inhibitors of the 11β-hydroxysteroid dehydrogenase-1. The compounds are useful for the treatment of diabetes, such as noninsulin-dependent diabetes (NIDDM), hyperglycemia, obesity, insulin resistance, dyslipidemia, hyperlipidemia, hypertension, Metabolic Syndrome, and other symptoms associated with NIDDM.

1 Claim, No Drawings

PYRAZOLE CARBOXAMIDES AS INHIBITORS OF 11-β-HYDROXYSTEROID DEHYDROGENASE-1

CROSS REFERENCE TO RELATED APPLICATIONS

This application is a U.S. national phase application under 35 USC §371 (c) based upon PCT application No. PCT/US2004/025036 filed on Aug. 3, 2004, which is related to U.S. provisional application Ser. No. 60/493,487 filed on Aug. 7, 2003, now lapsed, priority of which is claimed hereunder.

FIELD OF THE INVENTION

The present invention relates to pyrazole carboxamides as inhibitors of the enzyme 11-beta-hydroxysteroid dehydrogenase Type I (11β-HSD-1 or HSD-1) and methods of treating certain conditions using such compounds. The compounds of the present invention are useful for the treatment of diabetes, such as non-insulin dependent type 2 diabetes mellitus (NIDDM), insulin resistance, obesity, lipid disorders, hypertension, and other diseases and conditions.

BACKGROUND OF THE INVENTION

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

Persistent or uncontrolled hyperglycemia that occurs in diabetics is associated with increased morbidity and premature mortality. Abnormal glucose homeostasis is also associated both directly and indirectly with obesity, hypertension and alterations in lipid, lipoprotein and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy and retinopathy. Therefore, therapeutic control of glucose homeostasis, lipid metabolism, obesity and hypertension are critically important in the clinical management and treatment of diabetes mellitus.

Many patients who have insulin resistance but have not developed type 2 diabetes are also at a risk of developing symptoms referred to as "Syndrome X" or "Metabolic Syndrome". Syndrome X or Metabolic Syndrome is characterized by insulin resistance, along with abdominal obesity, hyperinsulinemia, high blood pressure, low HDL and high VLDL. These patients, whether or not they develop overt diabetes mellitus, are at increased risk of developing the cardiovascular complications listed above.

Treatment of type 2 diabetes typically includes physical exercise and dieting. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate insulin-resistant tissues. However, dangerously low levels of plasma glucose can result, and an increased level of insulin resistance can ultimately occur.

Biguanides increase insulin sensitivity, resulting in some correction of hyperglycemia. However, many biguanides, e.g., phenformin and metformin, cause lactic acidosis, nausea and diarrhea.

The glitazones (i.e. 5-benzylthiazolidine-2,4-diones) form a newer class of compounds with the potential for ameliorating hyperglycemia and other symptoms of type 2 diabetes. These agents substantially increase insulin sensitivity in muscle, liver and adipose tissue, resulting in partial or complete correction of the elevated plasma levels of glucose substantially without causing hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes. For a review of insulin-sensitizing agents and other mechanisms for the treatment of type 2 diabetes, see M. Tadayyon and S. A. Smith, "Insulin sensitisation in the treatment of type 2 diabetes," *Expert Opin. Investig. Drugs*, 12: 307-324 (2003).

There is a continuing need for new methods of treating diabetes and related conditions, such as Metabolic Syndrome. The present invention meets this and other needs.

SUMMARY OF THE INVENTION

The present invention relates to pyrazole carboxamides of structural formula I:

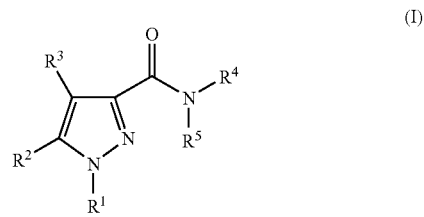

(I)

or a pharmaceutically acceptable salt or solvate thereof, wherein
each n is independently 0, 1, or 2;
$R^1$ is hydrogen or $C_{1-4}$ alkyl, wherein alkyl is unsubstituted or substituted with hydroxy or one to three fluorines;

$R^2$ is $C_{1-4}$ alkyl, aryl, arylmethyl, heteroaryl, or heteroarylmethyl, wherein aryl and heteroaryl are unsubstituted or substituted with one to four $R^6$ substituents;

$R^3$ is hydrogen, halogen, or $C_{1-4}$ alkyl, wherein alkyl is unsubstituted or substituted with hydroxy or one to three fluorines;

$R^4$ is hydrogen or $C_{1-4}$ alkyl;

$R^5$ is $(CH_2)_n$aryl, $(CH_2)_nC_{4-9}$ cycloalkyl, $(CH_2)_nC_{5-11}$ bicycloalkyl, or $(CH_2)_nC_{10-14}$ tricycloalkyl; wherein said aryl, cycloalkyl, bicycloalkyl, and tricycloalkyl are unsubstituted or substituted with one to three substituents independently selected from halogen, hydroxy, trifluoromethyl, and $C_{1-4}$ alkyl;

or $R^4$ and $R^5$ together with the nitrogen atom to which they are attached form a 5- to 7-membered ring saturated heterocycle optionally containing an additional heteroatom selected from O, S, and $NC_{0-4}$ alkyl wherein said heterocycle optionally fused with a benzene ring and wherein said heterocycle or optionally benzo-fused heterocycle is unsubstituted or substituted with one to three substituents independently selected from halogen, $C_{1-4}$ alkyl, trifluoromethyl, and $(CH_2)_n$aryl wherein aryl is unsubstituted or substituted with one to three substituents independently selected from halogen and $C_{1-4}$ alkyl;

or $R^4$ and $R^5$ together with the nitrogen atom to which they are attached form a $C_{6-11}$ azabicyclic ring system optionally containing an additional heteroatom selected from O, S, and $NC_{0-4}$ alkyl said azabicyclic ring being unsubstituted or substituted with one to three substituents independntly selected from halogen, hydroxy, and $C_{1-4}$ alkyl; and each $R^6$ is independently selected from the group consisting of: amino, $C_{1-4}$ alkylamino, di($C_{1-4}$ alkyl)amino, halogen, cyano, $C_{1-4}$ alkyl, hydroxy, $C_{1-4}$ alkoxy, $C_{1-4}$ alkylthio, $C_{1-4}$ alkylsulfonyl, trifluoromethyl, trifluoromethoxy, aryl, and heteroaryl;

wherein aryl and heteroaryl are unsubstituted or substituted with one to three substituents independently selected from cyano, halogen, hydroxy, $C_{1-4}$ alkoxy, $C_{1-4}$ alkyl, trifluoromethyl, and trifluoromethoxy.

The pyrazole carboxamides of the present invention are effective as inhibitors of 11β-hydroxysteroid dehydrogenase type 1(11β-HSD1). They are therefore useful for the treatment, control or prevention of disorders responsive to the inhibition of 11β-HSD1, such as type 2 diabetes, lipid disorders, obesity, atherosclerosis, and Metabolic Syndrome.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of 11β-HSD1 in a subject in need thereof by administering the compounds and pharmaceutical compositions of the present invention.

The present invention also relates to methods for the treatment or control of type 2 diabetes, obesity, lipid disorders, atherosclerosis, and Metabolic Syndrome by administering the compounds and pharmaceutical compositions of the present invention.

The present invention also relates to methods for treating obesity by administering the compounds of the present invention in combination with a therapeutically effective amount of another agent known to be useful to treat the condition.

The present invention also relates to methods for treating type 2 diabetes by administering the compounds of the present invention in combination with a therapeutically effective amount of another agent known to be useful to treat the condition.

The present invention also relates to methods for treating atherosclerosis by administering the compounds of the present invention in combination with a therapeutically effective amount of another agent known to be useful to treat the condition.

The present invention also relates to methods for treating lipid disorders by administering the compounds of the present invention in combination with a therapeutically effective amount of another agent known to be useful to treat the condition.

The present invention also relates to methods for treating Metabolic Syndrome by administering the compounds of the present invention in combination with a therapeutically effective amount of another agent known to be useful to treat the condition.

DETAILED DESCRIPTION OF THE INVENTION

The present invention is concerned with pyrazole carboxamide derivatives useful as inhibitors of 11β-HSD1. Compounds of the present invention are described by structural formula I:

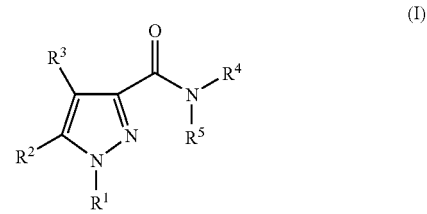

(I)

or a pharmaceutically acceptable salt or solvate thereof, wherein each n is independently 0, 1, or 2;

$R^1$ is hydrogen or $C_{1-4}$ alkyl, wherein alkyl is unsubstituted or substituted with hydroxy or one to three fluorines;

$R^2$ is $C_{1-4}$ alkyl, aryl, arylmethyl, heteroaryl, or heteroarylmethyl, wherein aryl and heteroaryl are unsubstituted or substituted with one to four $R^6$ substituents;

$R^3$ is hydrogen, halogen, or $C_{1-4}$ alkyl, wherein alkyl is unsubstituted or substituted with hydroxy or one to three fluorines;

$R^4$ is hydrogen or $C_{1-4}$ alkyl;

$R^5$ is $(CH_2)_n$aryl, $(CH_2)_nC_{4-9}$ cycloalkyl, $(CH_2)_nC_{5-11}$ bicycloalkyl, or $(CH_2)_nC_{10-14}$ tricycloalkyl; wherein said aryl, cycloalkyl, bicycloalkyl, and tricycloalkyl are unsubstituted or substituted with one to three substituents independently selected from halogen, hydroxy, trifluoromethyl, and $C_{1-4}$ alkyl;

or $R^4$ and $R^5$ together with the nitrogen atom to which they are attached form a 5- to 7-membered ring saturated heterocycle optionally containing an additional heteroatom selected from O, S, and $NC_{0-4}$ alkyl wherein said heterocycle optionally fused with a benzene ring and wherein said heterocycle or optionally benzo-fused heterocycle is unsubstituted or substituted with one to three substituents independently selected from halogen, $C_{1-4}$ alkyl, trifluoromethyl, and $(CH_2)_n$aryl wherein aryl is unsubstituted or substituted with one to three substituents independently selected from halogen and $C_{1-4}$ alkyl;

or $R^4$ and $R^5$ together with the nitrogen atom to which they are attached form a $C_{6-11}$ azabicyclic ring system optionally containing an additional heteroatom selected from O, S, and $NC_{0-4}$ alkyl said azabicyclic ring being unsubstituted or substituted with one to three substituents independntly selected from halogen, hydroxy, and $C_{1-4}$ alkyl; and each $R^6$ is independently selected from the group consisting of: amino, $C_{1-4}$ alkylamino, di($C_{1-4}$ alkyl)amino, halogen, cyano, $C_{1-4}$ alkyl, hydroxy, $C_{1-4}$ alkoxy, $C_{1-4}$ alkylthio, $C_{1-4}$ alkylsulfonyl, trifluoromethyl, trifluoromethoxy, aryl, and heteroaryl;

wherein aryl and heteroaryl are unsubstituted or substituted with one to three substituents independently selected from cyano, halogen, hydroxy, $C_{1-4}$ alkoxy, $C_{1-4}$ alkyl, trifluoromethyl, and trifluoromethoxy.

In one embodiment of the compounds of the present invention, $R^1$ is methyl. In a class of this embodiment, $R^3$ is hydrogen, halogen, or methyl. In a subclass of this class, $R^3$ is chlorine. In another subclass of this class, $R^3$ is methyl.

In a second class of this first embodiment, $R^2$ is aryl or heteroaryl, wherein aryl and heteroaryl are unsubstituted or substituted with one to three $R^6$ substituents. In a subclass of this class, $R^2$ is phenyl which is unsubstituted or substituted with one to three $R^6$ substituents. In another subclass of this class, $R^3$ is hydrogen, halogen, or methyl. In a subclass of this subclass, $R^3$ is chlorine. In another subclass of this subclass, $R^3$ is methyl.

In a second embodiment of the compounds of the present invention, $R^4$ is hydrogen or methyl and $R^5$ is $C_{4-9}$ cycloalkyl, $C_{5-11}$ bicycloalkyl or $C_{10-14}$ tricycloalkyl; wherein said cycloalkyl, bicycloalkyl, and tricycloalkyl are unsubstituted or substituted with one to three substituents independently selected from halogen, hydroxy, trifluoromethyl, and $C_{1-4}$ alkyl. In a class of this embodiment, $R^4$ is hydrogen. In a second class of this embodiment, $R^4$ is methyl. In a third class of this embodiment, $R^1$ is methyl; $R^2$ is aryl or heteroaryl, wherein aryl and heteroaryl are unsubstituted or substituted with one to three $R^6$ substituents; and $R^3$ is hydrogen, methyl or chlorine. In a subclass of this third class, $R^3$ is chlorine.

In a third embodiment of the compounds of the present invention, $R^4$ and $R^5$ together with the nitrogen atom to which they are attached form a 5- to 7-membered ring saturated heterocycle optionally containing an additional heteroatom selected from O, S, and $NC_{0-4}$ alkyl wherein said heterocycle optionally fused with a benzene ring and wherein said heterocycle or optionally benzo-fused heterocycle is unsubstituted or substituted with one to three substituents independently selected from halogen, $C_{1-4}$ alkyl, trifluoromethyl, and $(CH_2)_n$aryl wherein aryl is unsubstituted or substituted with one to three substituents independently selected from halogen and $C_{1-4}$ alkyl. In a class of this embodiment, $R^1$ is methyl; $R^2$ is aryl or heteroaryl, wherein aryl and heteroaryl are unsubstituted or substituted with one to three $R^6$ substituents; and $R^3$ is hydrogen, methyl or chlorine. In a subclass of this class, $R^3$ is chlorine or methyl.

In a fourth embodiment of the compounds of the present invention, $R^4$ and $R^5$ together with the nitrogen atom to which they are attached form a $C_{6-11}$ azabicyclic ring system optionally containing an additional heteroatom selected from O, S, and $NC_{0-4}$ alkyl said azabicyclic ring being unsubstituted or substituted with one to three substituents independntly selected from halogen, hydroxy, and $C_{1-4}$ alkyl. In a class of this embodiment, $R^1$ is methyl, $R^2$ is aryl or heteroaryl, wherein aryl and heteroaryl are unsubstituted or substituted with one to three $R^6$ substituents, and $R^3$ is hydrogen, methyl or chlorine. In a subclass of this class, $R^3$ is chlorine or methyl.

In a fifth embodiment of the compounds of the present invention, $R^1$ is methyl; $R^2$ is aryl or heteroaryl, wherein aryl and heteroaryl are unsubstituted or substituted with one to three $R^6$ substituents; $R^3$ is hydrogen, methyl or chlorine;

$R^4$ is hydrogen; and $R^5$ is adamantyl or bicyclo[2.2.1]heptyl, unsubstituted or substituted with one to three substituents independently selected from methyl, hydroxy, and halogen. In a class of thie embodiment, $R^3$ is chlorine.

Illustrative, but nonlimiting examples, of compounds of the present invention that are useful as inhibitors of 11-beta-hydroxysteroid dehydrogenase Type I are the following:

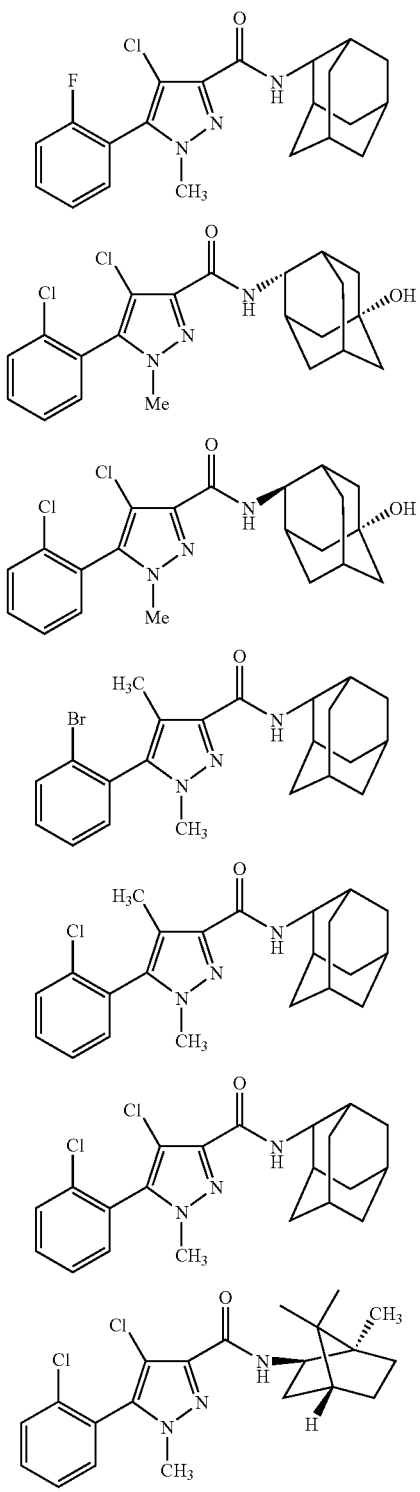

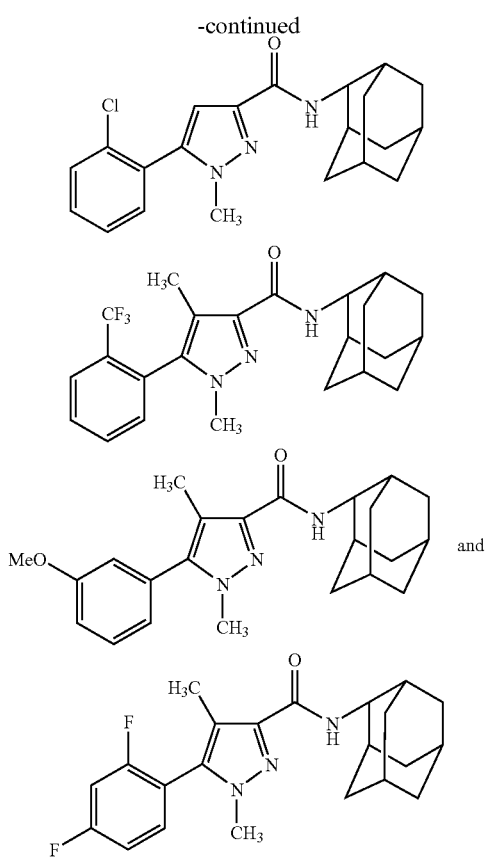

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Alkenyl" means carbon chains which contain at least one carbon-carbon double bond, and which may be linear or branched or combinations thereof, unless the carbon chain is defined otherwise. Examples of alkenyl include vinyl, allyl, isopropenyl, pentenyl, hexenyl, heptenyl, 1-propenyl, 2-butenyl, 2-methyl-2-butenyl, and the like. Where the specified number of carbon atoms permits, e.g., from $C_{5-10}$, the term alkenyl also includes cycloalkenyl groups, and combinations of linear, branched and cyclic structures. When no number of carbon atoms is specified, $C_{2-6}$ is intended.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl, and the like.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "bicycloalkyl" refers to a bridged alicyclic hydrocarbyl group containing one pair of bridgehead carbon atoms of the general structure

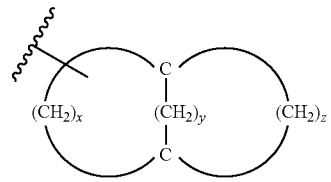

wherein x, y, and z are each independently 1, 2, or 3.

Representative examples of bicycloalkyl include, but are not limited to, bicyclo[2.1.1]hexyl, bicyclo[2.2.1]heptyl, bicyclo[2.2.2]octyl, and bicyclo[3.2.1]octyl of the respective formulae below:

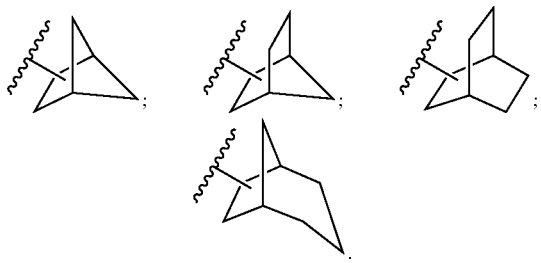

The term "tricycloalkyl" refers to a bridged alicyclic hydrocarbyl group possessing four bridgedhead carbons each common to three rings. A representative example of tricycloalkyl includes, but is not limited to, adamantyl, systematically named as tricyclo[$3.3.1^{1,5}.1^{3,7}$] of the formula below:

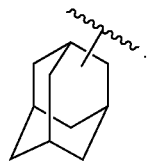

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkylsulfinyl" refers to straight or branched chain alkylsulfoxides of the number of carbon atoms specified (e.g., $C_{1-6}$ alkylsulfinyl), or any number within this range [i.e., methylsulfinyl (MeSO—), ethylsulfinyl, isopropylsulfinyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers, as well as mixtures thereof, are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

In a different aspect of the invention, a pharmaceutical composition is addressed comprising a compound in accordance with structural formula I, or a pharmaceutically acceptable salt or solvate thereof, in combination with a pharmaceutically acceptable carrier. By the term "solvate" is meant a hydrate, an alcoholate, or other solvate of crystallization.

In another aspect of the invention, a method of treating hyperglycemia, diabetes or insulin resistance in a mammalian patient in need of such treatment is addressed, which comprises administering to said patient an effective amount of a compound in accordance with structural formula I or a pharmaceutically salt or solvate thereof.

In another aspect of the invention, a method of treating non-insulin dependent diabetes mellitus is disclosed in a mammalian patient in need of such treatment comprising administering to the patient an anti-diabetic effective amount of a compound in accordance with structural formula I.

In another aspect of the invention, a method of treating obesity in a mammalian patient in need of such treatment is disclosed comprising administering to said patient a compound in accordance with structural formula I in an amount that is effective to treat obesity.

In another aspect of the invention, a method of treating Metabolic Syndrome in a mammalian patient in need of such treatment is disclosed, comprising administering to said patient a compound in accordance with structural formula I in an amount that is effective to treat Metabolic Syndrome.

In another aspect of the invention, a method of treating a lipid disorder selected from the group consisting of dyslipidemia, hyperlipidemia, hypertriglyceridemia, hypercholesterolemia, low HDL, and high LDL in a mammalian patient in need of such treatment is disclosed, comprising administering to said patient a compound in accordance with structural formula I in an amount that is effective to treat said lipid disorder.

In another aspect of the invention, a method of treating atherosclerosis in a mammalian patient in need of such treatment is disclosed, comprising administering to said patient a compound in accordance with structural formula I in an amount effective to treat atherosclerosis.

In another aspect of the invention, a method of treating a condition selected from the group consisting of: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia,

(10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment is disclosed, comprising administering to the patient a compound in accordance with structural formula I in an amount that is effective to treat said condition.

In another aspect of the invention, a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to delay the onset of said condition.

In another aspect of the invention, a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component in a mammalian patient in need of such treatment is disclosed, comprising administering to the patient a compound in accordance with structural formula I in an amount that is effective to reduce the risk of developing said condition.

In another aspect of the invention, a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other conditions and disorders where insulin resistance is a component, in a mammalian patient in need of such treatment, comprising administering to the patient an effective amount of a compound as defined in structural formula I and a compound selected from the group consisting of: (a) dipeptidyl peptidase-TV (DP-IV) inhibitors; (b) insulin sensitizing agents selected from the group consisting of (i) PPARγ agonists, (ii) PPARα agonists, (iii) PPARα/γ dual agonists, and (iv) biguanides; (c) insulin and insulin mimetics; (d) sulfonylureas and other insulin secretagogues; (e) α-glucosidase inhibitors; (f) glucagon receptor antagonists; (g) GLP-1, GLP-1 analogs, and GLP-1 receptor agonists; (h) GIP,GIP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid and salts thereof, (iv) inhibitors of cholesterol absorption, (v) acyl CoA:cholesterol acyltransferase inhibitors, and (vi) antioxidants; (k) PPARδ agonists; (l) antiobesity compounds; (m) ileal bile acid transporter inhibitors; (n) anti-inflammatory agents, excluding glucocorticoids; (o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan;

said compounds being administered to the patient in an amount that is effective to treat said condition.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001) and D. Spanswick and K. Lee, "Emerging antiobesity drugs," *Expert Opin. Emerging Drugs*, 8: 217-237 (2003).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; and U.S. Pat. No. 5,292,736.

Melanocortin receptor agonists that can be combined with compounds of structural formula I include those disclosed in WO 03/009847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists, *Expert Opin. Ther. Patents*, 12: 1631-1638 (2002).

In another aspect of the invention, a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment is disclosed, comprising administering to the patient a therapeutically effective amount of a compound as defined in structural formula I and an HMG-CoA reductase inhibitor.

More particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin.

Even more particularly, in another aspect of the invention, a method of treating a condition selected from the group consisting of hypercholesterolemia, atherosclerosis, low HDL levels, high LDL levels, hyperlipidemia, hypertriglyceridemia and dyslipidemia, in a mammalian patient in need of such treatment is disclosed, wherein the HMG-CoA reductase inhibitor is a statin selected from the group consisting of lovastatin, simvastatin, pravastatin, cerivastatin, fluvastatin, atorvastatin, itavastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound as defined in structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound as defined in structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin.

Even more particularly, a method for delaying the onset or reducing the risk of developing atherosclerosis in a human patient in need of such treatment is disclosed, wherein the HMG-Co A reductase inhibitor is a statin selected from the group consisting of: lovastatin, simvastatin, pravastatin, cerivastatin, fluvastatin, atorvastatin, itavastatin, and rosuvastatin.

Even more particularly, a method for delaying the onset or reducing the risk of developing atherosclerosis in a human patient in need of such treatment is disclosed, wherein the statin is simvastatin.

In another aspect of the invention, a method for delaying the onset or reducing the risk of developing atherosclerosis in a human patient in need of such treatment is disclosed, wherein the HMG-CoA reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises (1) a compound according to structural formula I, (2) a compound selected from the group consisting of: (a) DP-IV inhibitors; (b) insulin sensitizing agents selected from the group consisting of (i) PPARγ agonists; (ii) PPARα agonists, (iii) PPARα/γ dual agonists, and (iv) biguanides; (c) insulin and insulin mimetics; (d) sulfonylureas and other insulin secretagogues; (e) α-glucosidase inhibitors; (f) glucagon receptor antagonists; (g) GLP-1, GLP-1 analogs, and GLP-1 receptor agonists; (h) GIP, GP mimetics, and GIP receptor agonists; (i) PACAP, PACAP mimetics, and PACAP receptor 3 agonists; (j) cholesterol lowering agents selected from the group consisting of (i) HMG-CoA reductase inhibitors, (ii) sequestrants, (iii) nicotinyl alcohol, nicotinic acid or a salt thereof, (iv) inhibitors of cholesterol absorption, (v) acyl CoA:cholesterol acyltransferase inhibitors, and (vi) antioxidants; (k) PPARδ agonists; (l) antiobesity compounds; (m) ilcal bile acid transporter inhibitors; (n) anti-inflammatory agents other than glucocorticoids; (o) protein tyrosine phosphatase 1B (PTP-1B) inhibitors; and (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; (q) inhibitors of cholesteryl ester transfer protein (CETP); and (3) a pharmaceutically acceptable carrier.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

Solvates, and in particular, the hydrates of the compounds of structural formula I are included in the present invention as well.

The compounds described herein are selective inhibitors of the 11β-HSD1 enzyme. Thus, the present invention relates to the use of the 11β-HSD1 inhibitors for inhibiting the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance and hypertension. Administration of the compounds of the present invention decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension and dyslipidemia. Inhibition of 11β-HSD1 activity in the brain such as to lower cortisol levels may also be useful to treat or reduce anxiety, depression, and cognitive impairment.

The present invention includes the use of an 11β-HSD1 inhibitor for the treatment, control, amelioration, prevention, delaying the onset of or reducing the risk of developing the diseases and conditions that are described herein, as mediated by excess or uncontrolled amounts of cortisol and/or other corticosteroids in a mammalian patient, particularly a human, by the administration of an effective amount of a compound of structural formula I or a pharmaceutically acceptable salt or solvate thereof. Inhibition of the 11β-HSD1 enzyme limits the conversion of cortisone, which is normally inert, to cortisol, which can cause or contribute to the symptoms of these diseases and conditions if present in excessive amounts.

NIDDM and Hypertension:

The compounds of this invention are selective inhibitors of 11β-HSD1 over 11β-HSD2. While the inhibition of 11β-HSD1 is useful for reducing cortisol levels and treating conditions related thereto, inhibition of 11β-HSD2 is associated with serious side effects, such as hypertension.

Cortisol is an important and well recognized anti-inflammatory hormone, which also acts as an antagonist to the action of insulin in the liver, such that insulin sensitivity is reduced, resulting in increased gluconeogenesis and elevated levels of glucose in the liver. Patients who already have impaired glucose tolerance have a greater probability of developing type 2 diabetes in the presence of abnormally high levels of cortisol.

High levels of cortisol in tissues where the mineralocorticoid receptor is present often lead to hypertension. Inhibition of 11β-HSD1 shifts the ratio of cortisol and cortisone in specific tissues in favor of cortisone.

Administration of a therapeutically effective amount of an 11β-HSD1 inhibitor is effective in treating, controlling and ameliorating the symptoms of NIDDM, and administration of a therapeutically effective amount of an 11β-HSD 1 inhibitor on a regular basis delays or prevents the onset of NIDDM, particularly in humans.

Cushing's Syndrome:

The effect of elevated levels of cortisol is also observed in patients who have Cushing's Syndrome, which is a metabolic disease characterized by high levels of cortisol in the blood stream. Patients with Cushing's Syndrome often develop NIDDM.

Obesity, Metabolic Syndrome, Dyslipidemia:

Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Metabolic Syndrome, such as high blood pressure, elevated VLDL and reduced HDL. Montague et al., *Diabetes,* 2000, 49: 883-888. Thus, the administration of an effective amount of an 11β-HSD 1 inhibitor is useful in the treatment or control of obesity. Long-term treatment with an 11β-HSD1 inhibitor is also useful in delaying or preventing the onset of obesity, especially if the patient uses an 11β-HSD1inhibitor in combination with controlled diet and exercise.

By reducing insulin resistance and maintaining serum glucose at normal concentrations, compounds of the present invention also have utility in the treatment and prevention of conditions that accompany Type II diabetes and insulin resistance, including the Metabolic Syndrome or Syndrome X, obesity, reactive hypoglycemia and diabetic dyslipidemia.

Cognition and Dementia:

Excessive levels of cortisol in the brain may also result in neuronal loss or dysfunction through the potentiation of neurotoxins. Cognitive impairment has been associated with aging, and excess levels of cortisol in the brain. See J. R. Seckl and B. R. Walker, *Endocrinology,* 2001, 142: 1371-1376, and references cited therein. Administration of an effective amount of an 11β-HSD1 inhibitor results in the reduction, amelioration, control or prevention of cognitive impairment associated with aging and of neuronal dysfunction. Inhibitors of 11β-HSD1 may also be useful to treat anxiety and depression.

Atherosclerosis:

As described above, inhibition of 11β-HSD1 activity and a reduction in the amount of cortisol are beneficial in treating or controlling hypertension. Since hypertension and dyslipidemia contribute to the development of atherosclerosis, administration of a therapeutically effective amount of an 11β-HSD 1 inhibitor of the present invention may be especially beneficial in treating, controlling, delaying the onset of or preventing atherosclerosis.

Effects on Pancreas:

Inhibition of 11β-HSD1 activity in isolated murine pancreatic β-cells improves glucose stimulated insulin secretion (B. Davani et al., J. Biol. Chem., 2000, 275: 34841-34844). Glucocorticoids have been shown to reduce insulin secretion in vivo. (B. Billaudel et al., Horm. Metab. Res., 1979, 11: 555-560).

Reduction of Intraocular Pressure:

Recent data suggests a connection between the levels of glucocorticoid target receptors and the 11β-HSD enzymes and the susceptibility to glaucoma (J. Stokes et al., Invest. Ophthalmol., 2000, 41: 1629-1638). Therefore, inhibition of 11β-HSD1 activity is useful in reducing intraocular pressure in the treatment of glaucoma.

Immunomodulation:

In certain disease states, such as tuberculosis, psoriasis, and even under conditions of excessive stress, high glucocorticoid activity shifts the immune response to a humoral response, when in fact a cell based response may be more beneficial to the patient. Inhibition of 11β-HSD1 activity and the attendant reduction in glucocorticoid levels shifts the immune response toward a cell based response. See D. Mason, Immunology Today, 1991, 12: 57-60, and G. A. W. Rook, Baillièr's Clin. Endocrinol. Metab., 1999, 13: 576-581.

Osteoporosis:

Glucocorticoids can inhibit bone formation, which can result in a net bone loss. 11β-HSD1 has a role in bone resorption. Inhibition of 11β-HSD1 is beneficial in preventing bone loss due to osteoporosis. See C. H. Kim et al., J. Endocrinol., 1999, 162: 371-379; C. G. Bellows et al., Bone, 1998, 23: 119-125; and M. S. Cooper et al., Bone, 2000, 27: 375-381.

Other Utilities:

The following diseases, disorders and conditions can be treated, controlled, prevented or delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Metabolic Syndrome, (21) hypertension and other disorders where insulin resistance is a component.

The above diseases and conditions can be treated using the compounds of structural formula I, or the compound can be administered to prevent or reduce the risk of developing the diseases and conditions described herein. Since concurrent inhibition of 11β-HSD2 may have deleterious side effects or may actually increase the amount of cortisol in the target tissue where reduction of cortisol is desired, selective inhibitors of 11β-HSD1 with little or no inhibition of 11β-HSD2 are desirable.

The 11β-HSD1 inhibitors of structural formula I generally have an inhibition constant $IC_{50}$ of less than about 500 nM, and preferably less than about 100 nM. Generally, the $IC_{50}$ ratio for 11β-HSD2 to 11β-HSD1 of a compound is at least about two or more, and preferably about ten or greater. Even more preferred are compounds with an $IC_{50}$ ratio for 11β-HSD2 to 11β-HSD1 of about 100 or greater. For example, compounds of the present invention ideally demonstrate an inhibition constant $IC_{50}$ against 11β-HSD2 greater than about 1000 nM, and preferably greater than 5000 nM.

Compounds of structural formula I may be used in combination with one or more other drugs in the treatment, prevention, suppression or amelioration of diseases or conditions for which compounds of structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to: (a) dipeptidyl peptidase IV (DP-IV) inhibitors; (b) insulin sensitizing agents including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin; (c) insulin or insulin mimetics; (d) sulfonylureas and other insulin secretagogues such as tolbutamide, glipizide, meglitinide and related materials; (e) α-glucosidase inhibitors, such as acarbose; (f) glucagon receptor antagonists such as those disclosed in WO 98/04528, WO 99/01423, WO 00/39088 and WO 00/69810; (g) GLP-1, GLP-1 analogs, and GLP-1 receptor agonists such as those disclosed in WO00/42026 and WO00/59887; (h) GIP, GIP mimetics such as those disclosed in WO 00/58360, and GIP receptor agonists; (i) PACAP, PACAP mimetics, and PACAP receptor 3 agonists such as those disclosed in WO 01/23420; (j) cholesterol lowering agents such as (i) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as ezetimibe and beta-sitosterol, (v) acyl CoA:cholesterol acyltransferase inhibitors, such as, for example, avasimibe, and (vi) anti-oxidants, such as probucol; (k) PPARδ agonists, such as those disclosed in WO97/28149; (l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, and melanin-concentrating hormone (MCH) receptor antagonists; (m) ileal bile acid transporter inhibitors; (n) agents intended for use in inflammatory conditions other than glucocorticoids, such as aspirin, non-steroidal anti-inflammatory drugs, azulfidine, and selective cyclooxygenase-2 inhibitors; (o) protein tyrosine phosphatase 1B (PTP-1B) inhibitors; (p) antihypertensives including those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan; and (q) inhibitors of cholesteryl ester transfer protein (CETP). The above combinations include a compound of structural formula I, or a pharmaceutically acceptable salt or solvate thereof, with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors, and anti-obesity compounds.

Any suitable route of administration may be employed for providing a mammal, especially a human, with an effective dose of a compound of the present invention. For example, oral, rectal, topical, parenteral, ocular, pulmonary, nasal and the like may be employed. Dosage forms include tablets, troches, dispersions, suspensions, solutions, capsules, creams, ointments, aerosols and the like. Preferably the compound of structural formula I is administered orally.

The effective dosage of the active ingredient varies depending on the particular compound employed, the mode of administration, the condition being treated and the severity of the condition. Such dosages may be ascertained readily by a person skilled in the art.

When treating or preventing the diseases and conditions described herein, for which compounds of structural formula I are indicated, satisfactory results are obtained when the compounds of the invention are administered at a daily dosage of from about about 0.1 to about 100 milligram per kilogram (mpk) of body weight, preferably given as a single daily dose or in divided doses about two to six times a day. The total daily dosage thus ranges from about 0.1 mg to about 1000 mg, preferably from about 1 mg to about 50 mg. In the case of a typical 70 kg adult human, the total daily dose will range from about 7 mg to about 350 mg. This dosage may be adjusted to provide the optimal therapeutic response.

Another aspect of the present invention relates to a pharmaceutical composition which comprises a compound of structural formula I, or a pharmaceutically acceptable salt or solvate thereof, in combination with a pharmaceutically acceptable carrier.

The compositions include compositions suitable for oral, rectal, topical, parenteral (including subcutaneous, intramuscular, and intravenous), ocular (ophthalmic), transdermal, pulmonary (nasal or buccal inhalation), or nasal administration, although the most suitable route in any given case will depend on the nature and severity of the condition being treated and the active ingredient. They may be conveniently presented in unit dosage form and prepared by any of the methods well-known in the art of pharmacy.

The compound of structural formula I can be combined with the pharmaceutical carrier according to conventional pharmaceutical compounding techniques. Carriers take a wide variety of forms. For example, carriers for oral liquid compositions include, e.g., water, glycols, oils, alcohols, flavoring agents, preservatives, coloring agents and other components used in the manufacture of oral liquid suspensions, elixirs and solutions. Carriers such as starches, sugars and microcrystalline cellulose, diluents, granulating agents, lubricants, binders, disintegrating agents and the like are used to prepare oral solid dosage forms, e.g., powders, hard and soft capsules and tablets. Solid oral preparations are preferred over oral liquids.

The oral solid dosage forms may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. Capsules may also contain a liquid carrier such as a fatty oil.

Various other materials may be present to act as coatings or to modify the physical form of the dosage unit. For instance, tablets may be coated with shellac, sugar or both.

Tablets may be coated by standard aqueous or nonaqueous techniques. The typical percentage of active compound in these compositions may, of course, be varied from about 2 percent to about 60 percent on a w/w basis. Thus, tablets contain a compound of structural formula I or a salt or hydrate thereof in an amount ranging from as low as about 0.1 mg to as high as about 1.5 g, preferably from as low as about 1.0 mg to as high as about 500 mg, and more preferably from as low as about 10 mg to as high as about 100 mg.

Oral liquids such as syrups or elixirs may contain, in addition to the active ingredient, sucrose as a sweetening agent, methyl and propylparabens as preservatives, a dye and a flavoring such as cherry or orange flavor.

Parenterals are typically in the form of a solution or suspension, typically prepared with water, and optionally including a surfactant such as hydroxypropylcellulose. Dispersions can be prepared in glycerol, liquid polyethylene glycols and mixtures thereof in oils. Typically preparations that are in diluted form also contain a preservative.

The pharmaceutical injectable dosage forms, including aqueous solutions and dispersions and powders for the extemporaneous preparation of injectable solutions or dispersions, are also sterile and must be fluid to the extent that easy syringability exists; they must be stable under the conditions of manufacture and storage and are usually preserved. The carrier thus includes the solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants:

In vitro enzymatic activity was assessed for test compounds via a Scintillation Proximity Assay (SPA). In short, tritiated-cortisone substrate, NADPH cofactor and titrated compound were incubated with 11β-HSD1 enzyme at 37° C. to allow conversion to cortisol to progress. Following this incubation, a preparation of protein A coated SPA beads, pre-blended with anti-cortisol monoclonal antibody and a compound of structural formula I, was added to each well. The mixture was shaken at 15° C. and was then read on a liquid scintillation counter suitable for 96 well plates. Percent inhibition was calculated relative to a non-inhibited control well and $IC_{50}$ curves were generated. This assay was similarly applied to 11β-HSD2, whereby tritiated cortisol and NAD were used as the substrate and cofactor, respectively. To begin the assay, 40 μL of substrate (25 nM $^3$H-Cortisone+1.25 mM NADPH in 50 mM HEPES Buffer, pH 7.4) was added to designated wells on a 96-well plate. The compound was dissolved in DMSO at 10 mM followed by a subsequent 50 fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 μL of SPA beads, pre-suspended with anti-cortisol monoclonal antibody and a compound of formula I, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1-25 nM $^3$H cortisol was added to designated single wells. 1 μL of 200 μM compound was added to each of these wells, along with 10 μL of buffer instead of enzyme. Any calculated inhibiton was due to compound interfering with the cortisol binding to the antibody on the SPA beads.

Assays: Measurement of In Vivo Inhibition:

In general terms, the test compound was dosed orally to a mammal and a prescribed time interval was allowed to elapse, usually between 1 and 24 h. Tritiated cortisone was injected intravenously, followed several min later by blood collection. Steroids were extracted from the separated serum and analyzed by HPLC. The relative levels of $^3$H-cortisone and its reduction product, $^3$H-cortisol, were determined for the compound and vehicle-dosed control groups. The absolute conversion, as well as the percentage of inhibition, was calculated from these values.

More specifically, compounds were prepared for oral dosing by dissolving them in vehicle (5% hydroxypropyl-beta-cyclodextrin v/v $H_2O$, or equivalent) at the desired concentration to allow dosing at typically 10 mg per kg. Following an overnight fasting, the solutions were dosed to ICR mice (obtained from Charles River) by oral gavage, 0.5 mL per dose per animal, with three animals per test group.

After the desired time had passed, routinely either 1 or 4 h, 0.2 mL of 3 µM $^3$H-cortisone in dPBS was injected by tail vein. The animal was caged for two min followed by euthanasia in a $CO_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum, they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to $^3$H-cortisol was calculated as the ratio of AUC for cortisol over the combined AUC for cortisone and cortisol.

Preparation of Compounds of the Invention:

The compounds of structural formula I of the present invention can be prepared according to the procedures of the following Schemes and Examples, using appropriate materials and are further exemplified by the following specific examples. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the their neutral form, but the triazole moeity can be further converted into a pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electrospray ion-mass spectroscopy (ESMS).

Reaction Schemes 1 and 2 illustrate the methods employed in the synthesis of the compounds of the present invention of structural formula I. All substituents are as defined above unless indicated otherwise.

Reaction Scheme 1 illustrates a general synthesis of the novel compounds of structural formula I of the present invention. As shown in Scheme 1, an acetophenone 1-1, which may be variously substituted on the aromatic ring ($R^6$) and for which $R^3$ is hydrogen, methyl or short alkyl, can be carboxylated by treating with a strong base such as lithium hexamethyldisilazide (LiHMDS) or lithium diisopropylamide (LDA) followed by an oxalate diester in order to provide an α,γ-diketoester 1-2. Intermediate 1-2 can be converted to a pyrazole 1-3 by heating with $R^1$-hydrazine, followed by hydrolysis of the ester. Weak acid catalysts, such as acetic acid, facilitate the pyrazole forming reaction. The hydrolysis of the ester may be accomplished in a variety of ways well known to those skilled in the art, with sodium or potassium hydroxide in aqueous methanol/tetrahydrofuran being a common and generally useful set of conditions. Intermediate 1-3 can be subjected to any of a variety of amide coupling conditions well known to those skilled in art with primary or secondary amines, to provide amides such as 1-5 of structural formula I. For intermediates 1-3 in which $R^3$ is hydrogen, $R^3$ may be transformed to Cl prior to the amide forming reaction, resulting in amides of formula 1-6, another subset of amides of structural formula I. A variety of electrophilic chlorinating reagents can be used for this transformation, including but not limited to molecular chlorine and N-chlorosuccinimide.

Scheme 1

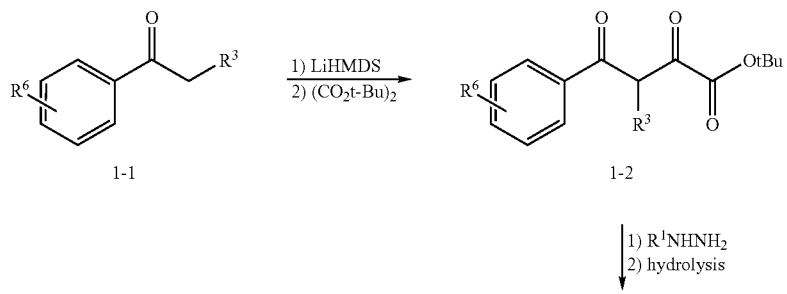

-continued

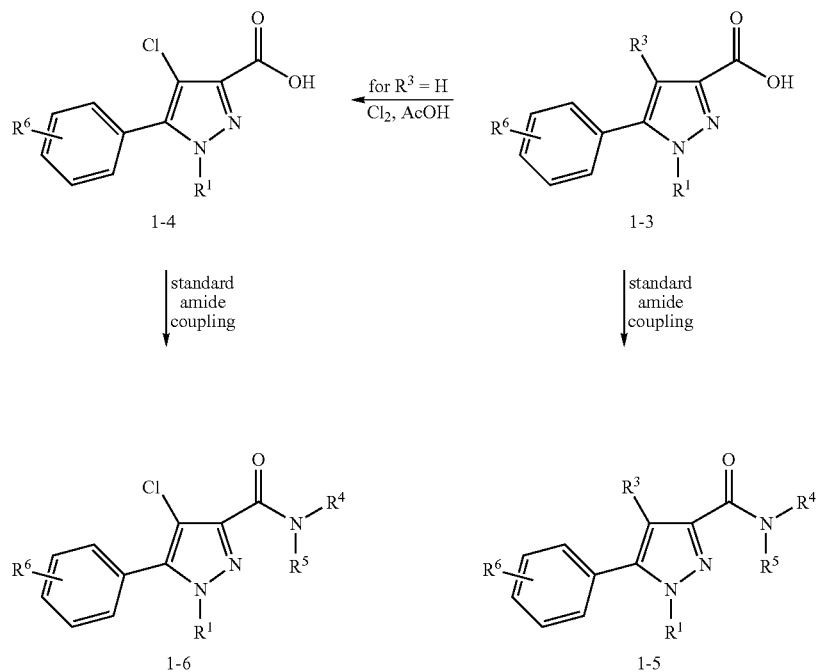

Reaction Scheme 2 represents an alternative general synthesis of compounds of structural formula I. In this procedure, a hydroxypyrazole 2-2 is prepared from a ketodiester of formula 2-1, (R=Me or Et) using $R^1$-hydrazine followed by ester hydrolysis as described above. Intermediate 2-2 can be treated with triflic anhydride in pyridine, followed by a primary or secondary amine, to produce a trifloxypyrazine amide of formula 2-3. This trifloxypyrazine 2-3 can be coupled with arylboronic acids using the Suzuki reaction to produce compounds 2-4 of structural formula I. A variety of palladium catalysts can be used in the Suzuki reaction, including but not limited to $Pd(PPh_3)_4$ and $Pd(OAc)_2/PPh_3$.

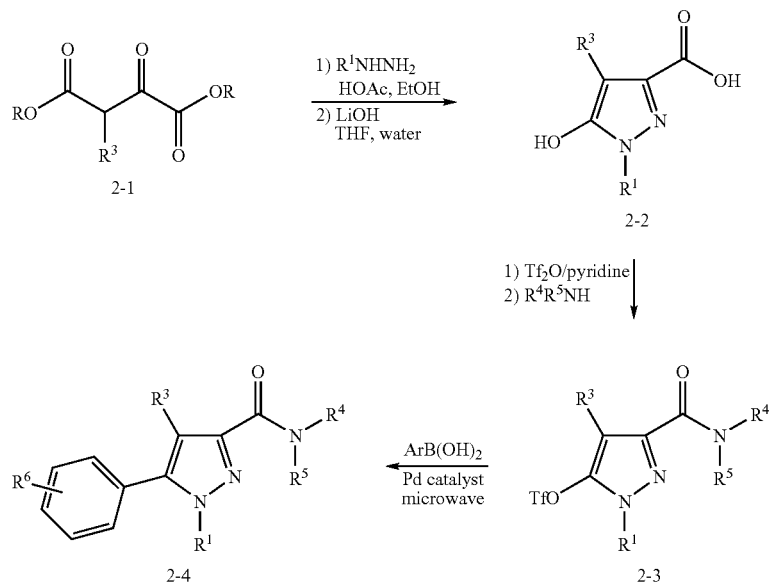

Scheme 2

The following Examples are provided to illustrate the invention and are not to be construed as limiting the scope of the invention in any manner.

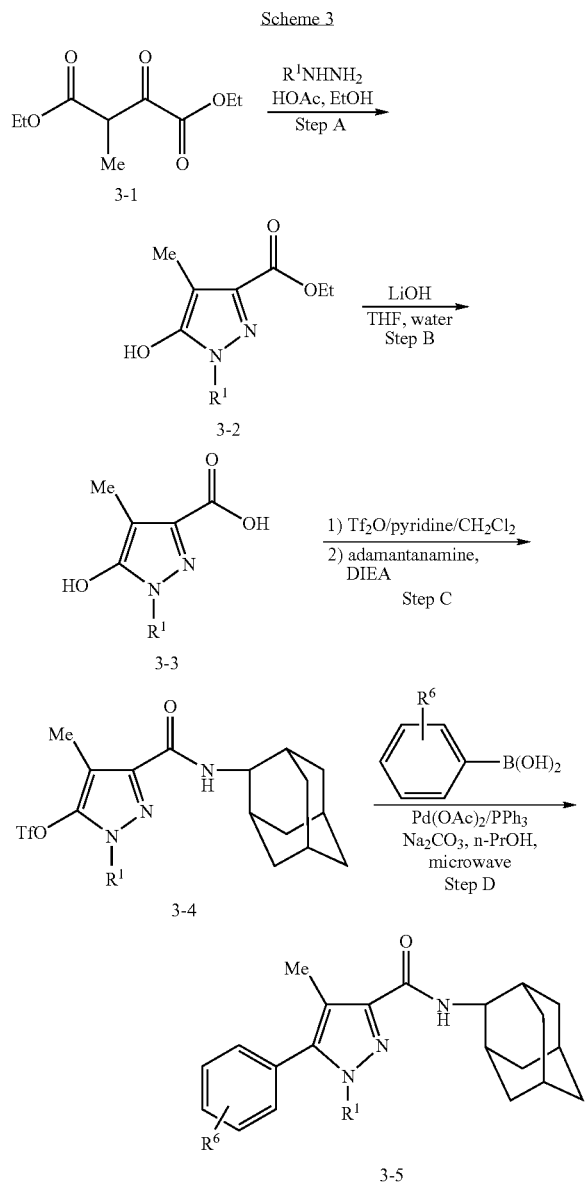

Step A:
To a magnetically stirred solution of diethyl oxalpropionate (3-1) (10.04 g, 49.65 mmol) in ethanol (50 mL) and acetic acid (10 mL) under a nitrogen atmosphere was added methylhydrazine (3.4 mL, 1.3 eq). The mixture was heated to reflux for two days. After this time the solvent was removed under reduced pressure and hexane with some ethyl acetate was added. The product 3-2 crystallized and the solid was filtered, washed and dried.

Step B:
To a magnetically stirred solution of ester 3-2 (5.50 g, 29.86 mmol) in THF (100 mL) was added water (50 mL) and LiOH monohydrate (5.00 g, 4 eq). After several hours the reaction was acidified to pH about 5 with concentrated HCl and extracted three times with THF. The combined organic layers were dried over MgSO$_4$, filtered and the solvent removed under reduced pressure to give acid 3-3.

Step C:
To a magnetically stirred solution of acid 3-3 (502 mg, 3.22 mmol) in dichloromethane (50 mL) under a nitrogren atmosphere was added pyridine (3.2 mL, 12 eq). The reaction mixture was cooled to 0° C. in an ice bath. To the reaction mixture was added trifluoromethanesulfonic anhydride (3.3 mL, 6 eq). After 30 min the bath was removed and the reaction warmed to room temperature for 2 h. To the reaction mixture was added 2-adamantanamine hydrochloride (1.21 g, 2 eq) and the reaction mixture was allowed to stir overnight. After this time the reaction mixture was diluted with dichloromethane and washed twice with water followed by 1% aqueous HCl and saturated aqueous brine solution. The organic layer was dried over MgSO$_4$, filtered and the solvent removed under reduced pressure. The residue was purified by silica chromatography eluting with 5% EtOAc/hexane to afford the triflate amide product 3-4.

Step D:
The above triflate amide (84.4 mg, 0.200 mmol) was dissolved in degassed n-propanol (1 mL) and added to a microwave tube containing the appropriately substituted phenylboronic acid (1.4-1.5 eq), triphenylphosphine (about 50 mol %) and palladium acetate (about 25 mol %). A stir bar was added and the vessel was flushed with nitrogen gas, crimp sealed, and heated in the microwave at 120° C. for 2 min. Methanol was added to the reaction to precipitate solids and these were filtered off through a silica plug. The solvent of the filtrate was removed under reduced pressure. The residue was taken up in dichloromethane and washed with 0.5 N sodium hydrogencarbonate. The organic layer was dried over MgSO$_4$, filtered and the solvent removed under reduced pressure. Purification was accomplished by silica chromatography, usually Biotage QUAD3. Final products were lyophilized from acetonitrile/water.

Scheme 4

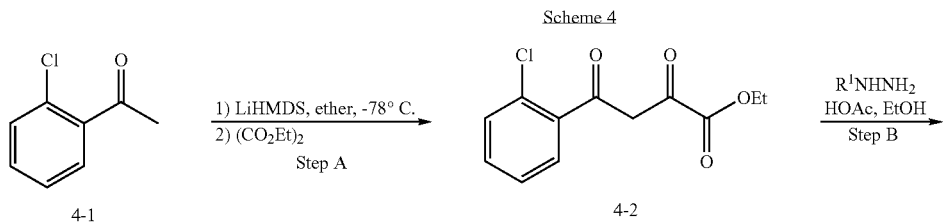

-continued

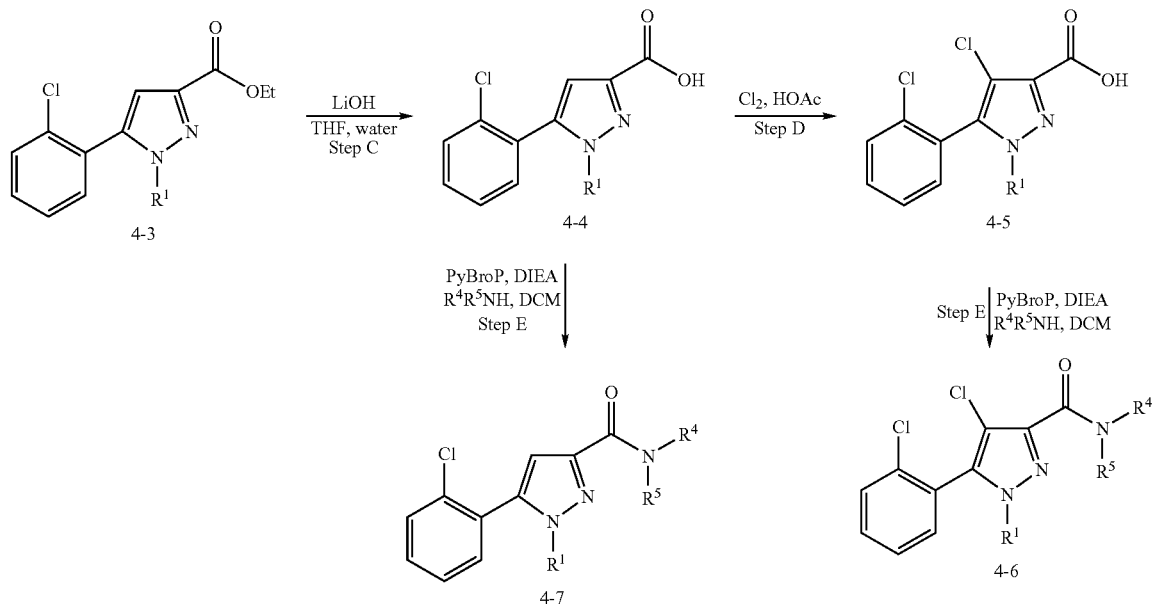

Step A:

In a 500 mL round bottom flask was added anhydrous diethyl ether (250 mL) and a stir bar. The vessel was sealed, flushed with nitrogen gas and cooled to −78° C. in a dry ice acetone bath. Lithium hexamethyldisilazide (1.0 M in hexane, 78 mL, 78 mmol) was added and the solution allowed to cool 15 min. Ortho-chloroacetophenone 4-1 (10 mL, 1 eq) was added and the solution allowed to stir cold for 1 h. Diethyl oxalate (12.5 mL, 1.2 eq) was added and the reaction warmed up overnight. The product 4-2 was filtered off and dried.

Step B:

To a magnetically stirred solution of 4-2 (1.05 g, 4.01 mmol) and ethanol (20 mL) was added glacial acetic acid (5 mL). The vessel was flushed with nitrogen gas. Methylhydrazine ($R^1$=Me) (260 μL, 1.2 eq) was added and the reaction mixture allowed to stir overnight. Two products are formed. The more polar isomer was the desired product. The solvent was removed under reduced pressure and the residue taken up in EtOAc. The acid was neutralized with saturated sodium hydrogencarbonate solution and then the organic layer was washed with water and saturated brine. The organic layer was dried over $MgSO_4$ and filtered. Purification was accomplished by silica chromatography eluting with 15-50% EtOAc/hexane to afford the desired product 4-3.

Step C:

To a magnetically stirred solution of pyrazole 4-3 (736.4 mg, 2.789 mmol) in THF (50 mL) and water (10 mL) was added lithium hydroxide monohydrate (1.20 g, 10 eq). The solution was refluxed for 2.5 h. The solvent was removed under reduced pressure. The residue was taken up in EtOAc, acidified with 1 N HCl and extracted twice with EtOAc. The combined organic layers were dried over $MgSO_4$ and filtered. The product 4-4 was dried thoroughly.

Step D:

Through a magnetically stirred solution of acid 4-4 (340 mg, 1.44 mmol) in HOAc (10 mL) was bubbled chlorine gas for 15 min. The solvent was removed under reduced pressure and the residue taken up in EtOAc and water. The product was extracted twice from water and the combined organic layers were dried over $MgSO_4$ and filtered. The product 4-5 was evaporated from diethyl ether to give a solid.

Step E:

To a magnetically stirred solution of 4-4 or 4-5 (28 mg) in DCM (1 mL) was added DIEA (6 eq) and PyBroP (1.3 eq). The solution was allowed to stir 20 min and then amine $R^4R^5NH$ (1.2 eq) was added. The solution was allowed to stir overnight. Purification was accomplished by silica chromatography eluting with EtOAc/hexane to afford compounds 4-6 and 4-7 of structural formula I.

Scheme 5

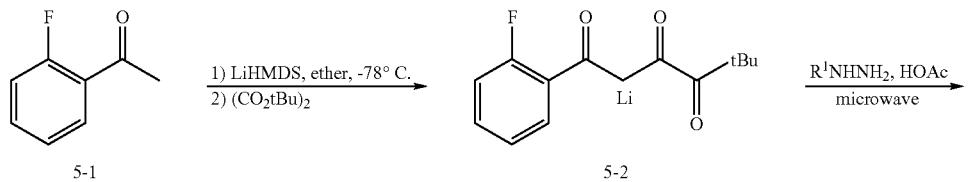

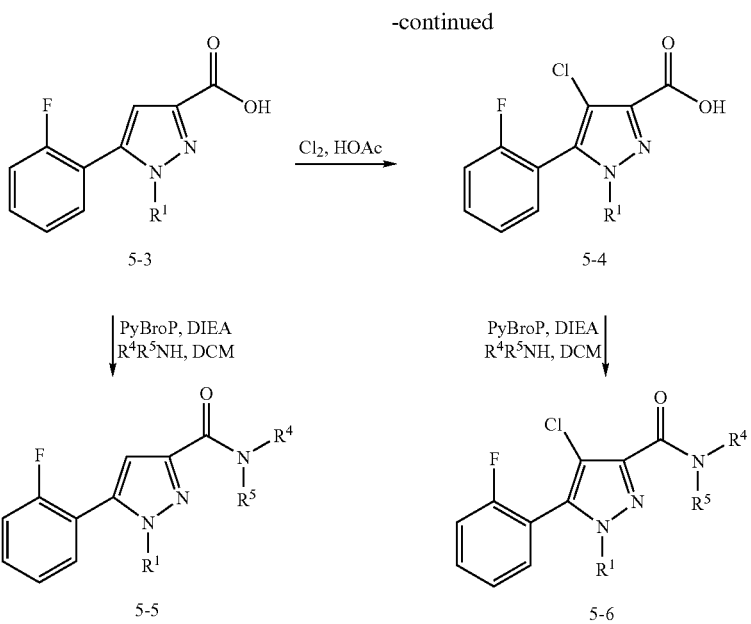

Step A:

In a 500 mL round bottom flask was added anhydrous diethyl ether (250 mL) and a stir bar. The vessel was sealed, flushed with nitrogen gas and cooled to −78° C. in a dry ice acetone bath. Lithium hexamethyldisilazide (1.0 M in hexane, 78 mL, 78 mmol) was added and the solution allowed to cool for 15 min. Ortho-fluoroacetophenone 5-1 (10 mL, 1 eq) was added and the solution allowed to stir cold for 1 h. Di-t-butyl oxalate (19.7 g, 1.2 eq) was added and the reaction warmed up overnight. The product 5-2 was filtered off and dried thoroughly.

Step B:

To a solution of 5-2 (1 g, 3.66 mmol) in HOAc (5 mL) was added methylhydrazine ($R^1$=Me) (234 μL, 1.2 eq) in a microwave tube. The tube was flushed with nitrogen gas and sealed. The reaction was heated in the microwave at 150° C. for 20 min. The solvent was removed under reduced pressure to a white solid. The desired isomer was more polar and less soluble than the other isomer. The residue was taken up in EtOAc and the desired isomer filtered off. To recover the rest of the product 5-3, the remaining filtrate was purified by silica chromatography eluting with 200:100:10:2/DCM:hexane: methanol:HOAc collecting the lower isomer. Compound 5-3 was converted into intermediate 5-4 and into final compounds 5-5 and 5-6 following the procedures detailed above for the preparation of compounds 4-6 and 4-7.

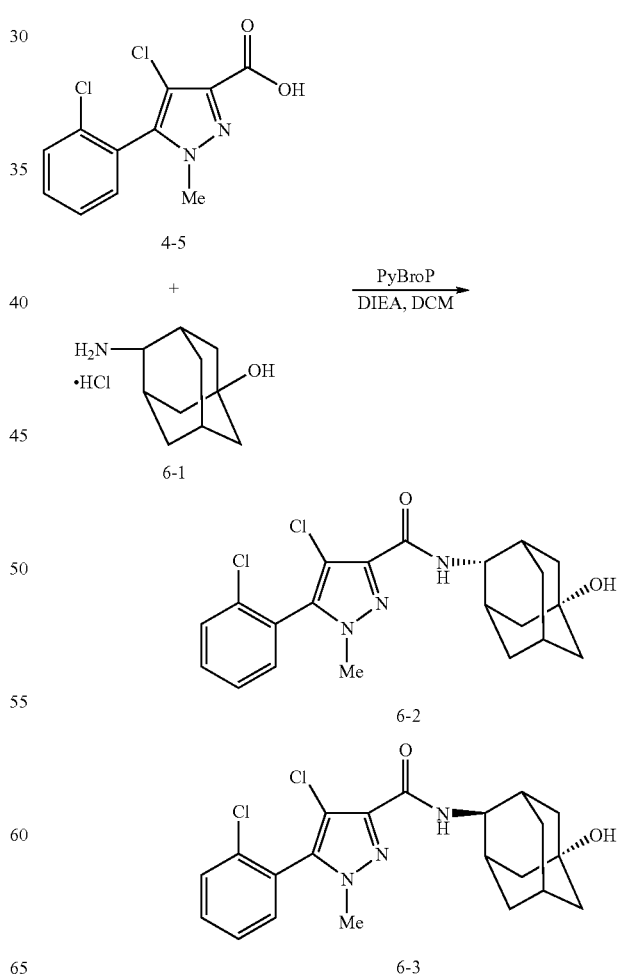

Scheme 6

EXAMPLES 1 and 2

To a magnetically stirred solution of intermediate 4-5 (25 mg, 0.092 mmol) in DCM (1 mL) was added DIEA (6 eq) and PyBroP (1.3 eq). The solution was allowed to stir for 10 min and then hydroxyadamantanamine hydrochloride (6-1) (1.2 eq) was added. The solution was allowed to stir overnight. Two isomers, cis and trans, (6-2 and 6-3, respectively) were formed. Purification was accomplished by silica gel chromatography eluting with 80%/EtOAc:hexane. Overlapping fractions were purified by further silica gel chromatography under the same eluent conditions. A final purification of each isomer was performed on C-18 reverse phase. The final products were extracted with DCM from saturated aqueous sodium hydrogencarbonate solution. The organic layer was dried over $MgSO_4$ and filtered and the filtrate evaporated to afford the final compounds. Mass spectrum: m/z 420.1 (M+H).

More nonpolar, cis compound 6-2:

$^1$H NMR (CDCl$_3$, 600 MHz) 7.57 (d, J=8.0 Hz, 1H), 7.49 (td, J=7.7 Hz, J=2.3 Hz, 1H), 7.43 (t, J=7.0 Hz, 1H), 7.33 (dd, J=7.6 Hz, J=1.7 Hz, 1H), 7.15 (d, J=7.8 Hz, 1H), 4.17 (d, J=8.1 Hz, 1H), 3.73 (s, 3H), 2.34 (s, 2H), 2.18 (s, 1H), 1.93 (d, J=12 Hz, 2H), 1.81 (d, J=12.8 Hz, 2H), 1.75 (m, 4H), 1.66 (d, J=12.6 Hz, 2H);

More polar, trans compound 6-3:

1H NMR (CDCl3, 600 MHz) 7.57 (d, J=7.5 Hz, 1H), 7.49 (td, J=7.9 Hz, J=1.7 Hz, 1H), 7.43 (td, J=7.6 Hz, J=1.1 Hz, 1H), 7.33 (dd, J=7.5 Hz, J=1.6 Hz, 1H), 7.11 (d, J=7.6 Hz, 1H), 4.25 (d, J=7.8 Hz, 1H), 3.74 (s, 3H), 2.28 (s, 2H), 2.21 (s, 1H), 1.95 (d, J=11.6 Hz, 2H), 1.87 (d, J=13.6 Hz, 2H), 1.81 (m, 4H), 1.56 (m, 2H).

The following additional Examples were prepared according to the general methods described above:

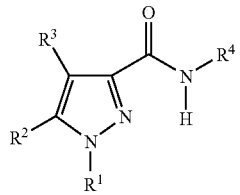

(Ia)

| Ex. | $R^1$ | $R^2$ | $R^3$ | $R^4$ | Parent Ion m/z (M + H) |
|---|---|---|---|---|---|
| 3 | Me | 2-F-phenyl | Cl | adamantyl | 388.2 |
| 4 | Me | 2-Br-phenyl | Me | adamantyl | 428.2 |
| 5 | Me | 2-Cl-phenyl | Me | adamantyl | 384.2 |
| 6 | Me | 2-Cl-phenyl | Cl | adamantyl | 404.2 |
| 7 | Me | 2-Cl-phenyl | Cl | bornyl | 406.2 |

-continued
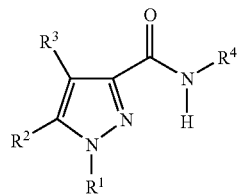
(Ia)
| Ex. | R¹ | R² | R³ | R⁴ | Parent Ion m/z (M + H) |
|---|---|---|---|---|---|
| 8 | Me | 2-Cl-phenyl | H | 2-adamantyl | 370.3 |
| 9 | Me | 2-CF₃-phenyl | Me | 2-adamantyl | 418.3 |
| 10 | Me | 3-OMe-phenyl | Me | 2-adamantyl | 380.3 |
| 11 | Me | 2,4-di-F-phenyl | Me | 2-adamantyl | 386.3 |
| 12 | Me | benzothiophen-2-yl | Me | 2-adamantyl | 406.3 |
| 13 | Me | 2-Me-phenyl | Me | 2-adamantyl | 364.3 |
| 14 | Me | benzo[1,3]dioxol-5-yl | Me | 2-adamantyl | 394.2 |

-continued
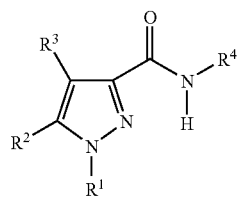
(Ia)
| Ex. | R¹ | R² | R³ | R⁴ | Parent Ion m/z (M + H) |
|---|---|---|---|---|---|
| 15 | Me | 2-F-phenyl | Cl | 2-adamantyl | 388.2 |
| 16 | Me | 4-OCF₃-phenyl | Cl | 2-adamantyl | 454.2 |
| 17 | Me | 2-Cl-phenyl | Cl | 2-(trifluoromethyl)benzyl | 428.2 |
| 18 | CH(CH3)2 | 4-Cl-phenyl | Me | 2-adamantyl | 412.1 |
| 19 | CH₂CF₃ | 4-Cl-phenyl | Me | 2-adamantyl | 452.2 |
| 20 | H | 4-Cl-phenyl | Cl | 2-adamantyl | 390.1 |
| 21 | Me | Benzyl | Me | 2-adamantyl | 364.4 |

EXAMPLE OF A PHARMACEUTICAL FORMULATION

As a specific embodiment of an oral composition of a compound of the present invention, 50 mg of the compound of Example 1 or 2 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention.

What is claimed is:

1. A compound of structural formula I:

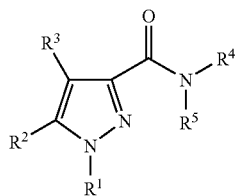

(I)

or a pharmaceutically acceptable salt thereof, wherein
each n is independently 0, 1, or 2;

$R^1$ is methyl;

$R^2$ is aryl or heteroaryl, or heteroarylmethyl, wherein aryl and heteroaryl are unsubstituted or substituted with one to four $R^6$ substituents;

$R^3$ is hydrogen, chlorine, or methyl;

$R^4$ and $R^5$ together with the nitrogen atom to which they are attached form a 5- to 7-membered ring saturated heterocycle optionally containing an additional heteroatom selected from O, S, and $NC_{0-4}$ alkyl wherein said heterocycle optionally fused with a benzene ring and wherein said heterocycle or optionally benzo-fused heterocycle is unsubstituted or substituted with one to three substituents independently selected from halogen, $C_{1-4}$ alkyl, trifluoromethyl, and $(CH_2)_n$aryl wherein aryl is unsubstituted or substituted with one to three substituents independently selected from halogen and $C_{1-4}$ alkyl; and each $R^6$ is independently selected from the group consisting of: amino, $C_{1-4}$ alkylamino, di($C_{1-4}$ alkyl)amino, halogen, cyano, $C_{1-4}$ alkyl, hydroxy, $C_{1-4}$ alkoxy, $C_{1-4}$ alkylthio, $C_{1-4}$ alkylsulfonyl, trifluoromethyl, trifluoromethoxy, aryl, and heteroaryl;

wherein aryl and heteroaryl are unsubstituted or substituted with one to three substituents independently selected from cyano, halogen, hydroxy, $C_{1-4}$ alkoxy, $C_{1-4}$ alkyl, trifluoromethyl, and trifluoromethoxy.

* * * * *